United States Patent [19]

Jung et al.

[11] Patent Number: 5,302,734
[45] Date of Patent: Apr. 12, 1994

[54] 1,3-DISILACYCLOBUTANES AND THE METHOD FOR PRODUCING THEREOF

[75] Inventors: Il Nam Jung; Gyu-Hwan Lee, both of Seoul; Jang-Hwan Hong; Seung Ho Yeon, both of Kyungki-Do, all of Rep. of Korea

[73] Assignee: Korea Institute of Science and Technology, Seoul, Rep. of Korea

[21] Appl. No.: 897,470

[22] Filed: Jun. 11, 1992

[30] Foreign Application Priority Data

Jun. 14, 1991 [KR] Rep. of Korea .................. 9858/1991

[51] Int. Cl.$^5$ .............................................. C07F 7/08
[52] U.S. Cl. .................................................... 556/406
[58] Field of Search ....................................... 556/406

[56] References Cited

U.S. PATENT DOCUMENTS

| | | | |
|---|---|---|---|
| 2,850,514 | 9/1958 | Knoth | 556/406 X |
| 3,178,392 | 4/1965 | Kriner | 556/406 X |
| 4,328,350 | 5/1982 | Guselnikov et al. | 556/406 |

OTHER PUBLICATIONS

Fritz, G., et al., "Carbosilanes, Syntheses and Reactions," Springer-Verlag, New York (1986).
Knoth, Jr., W. H., et al., "1,1,3,3-Tetramethyl-1,3-disilacyclobutane," *J. Org. Chem.* 23:1392–1393 (1958).
Auner, N., et al., "Preparation and Characterization of 1,3-disilacyclobutanes," *J. Organomet. Chem.*, 188 (2):151–177 (1980); *Chem. Abs.*, 93:26500 (1980).
Nametkin, N. S., et al., "Formation of 1,3-disilacyclobutanes," *Izv. Akad. Nauk SSSR, Ser. Khim.*, 3:584–585 (1966); *Chem. Abs.*, 65:5478e (1966).
Jones, P. R., et al., "The Addition of tert-Butyllithium to Vinylhalosilanes: A Novel, High Yield Route to 1,3-Disilacyclobutanes," *J. Am. Chem. Soc.*, 99:2013–2015 (1977).
Barton, T. J., et al., "New Silene Rearrangements from a Study of the Mechanism of Silacyclopentene Formation from [3.3] Silaspirocycloheptane," *Organometallics*, 2:8–11 (1983).
Noll, W., "Chemistry and Technology of Silicones," Academic Press, New York (1968).
Barton, T. J., et al., "Generation and Trapping of 6,6-Dimethyl-6-Silafulvene," *Tetrahedron Lett.*, 22:7–10 (1981).

*Primary Examiner*—Paul F. Shaver
*Attorney, Agent, or Firm*—Townsend and Townsend Khourie and Crew

[57] ABSTRACT

The present invention relates to a process for preparing 1,3-disilacyclotutanes by pyrolyzing alkoxytrisilaalkaness at a temperature of from 400° C. to 800° C. at the atmospheric pressure or under the vacuum. This is a new synthetic route of 1,3-disilacyclobutanes which employs readily available starting materials without using alkaline metals or magnesium, affords very good yields, produces very clean product mixtures separable by distillation, and tolerates functionality on silicon.

4 Claims, No Drawings

1,3-DISILACYCLOBUTANES AND THE METHOD FOR PRODUCING THEREOF

BACKGROUND OF THE INVENTION

1. Field of the Invention

The present invention relates to 1,3-disilacyclobutanes as represented by the formula (I) and to a process for preparing 1,3-disilacyclobutanes as represented in formula (I) by pyrolyzing alkoxytrisilaalkanes as represented in formula (II).

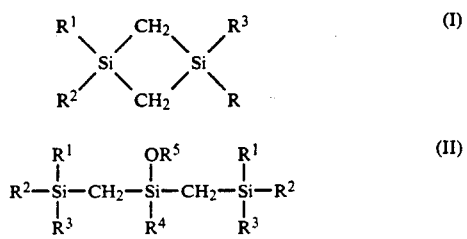

wherein, $R^1$, $R^2$, $R^3$ and $R^4$ and $R^5$ may be the same or different and represent methyl, methoxy, phenyl, or chlorine atom.

The pyrolysis of alkoxytrisilaalkanes at a temperature from 400° C. to 800° C. at atmospheric pressure or under a vacuum gives silenes through beta elimination of alkoxysilanes and followed by an intramolecular 1,5-hydrogen shift of the resulting silenes and ring closure of the biradicals. The pyrolysis of alkoxytrisilaalkanes having functional groups on silicon such as phenyl, alkoxy, and chloro substituent gives 1,3-disilacyclobutanes which are able to tolerate the functional groups. The products can be easily separated from the product mixture by distillation.

DESCRIPTION OF THE PRIOR ART

Carbosilanes having the elements silicon and carbon alternately in the molecular-skeleton are the most important starting materials for silicon carbide products (G. Fritz and E. Martern, "Carbosilanes, Syntheses and Reactions", Springer-Verlag, New York, 1986).

1,3-disilacyclobutanes contain a strained ring that is opened easily under the conditions of thermolysis or photolysis. The action of various transition metal complexes on 1,3-disilacyclobutanes results in ring opening polymerization. Knoth reported in U.S. Pat. No. 2,483,972 that $H_2Pt\ Cl_6$ was particularly effective for the ring opening polymerization. (W. H. Knoth Jr., U.S. Pat. No. 2,483,972).

Knoth and Lindsey first reported 1,3-disilacyclobutanes prepared from 1-chloro-4-fluoro-2,2,3-trimethyl-2,4-disilapentane and magnesium metal in 1958 (W. H. Knoth Jr. and R. V. Lindsey Jr., J. Org. Chem., 1958, 23, 1392).

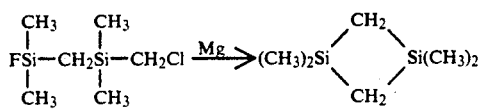

1,3-disilacyclobutanes are generally prepared by two methods. One is the metalation of chloromethylchlorosilanes using potassium or magnesium followed by coupling reactions. The other is the generation of silenes by pyrolyzing monosilacyclobutanes followed by dimerization of the resulting silenes.

In 1980, Auner and his co-workers reported the preparation of 1,3-disilacyclobutanes by metalating chloromethyl containing chlorosilanes with magnesium or potassium in ether solution. The chloromethyl group is dechlorinated by metals and the resulted carbanion is coupled with chlorosilanes. The chloromethylchlorosilanes are commercially available or readily prepared by the chlorination of the corresponding methylchlorosilanes. However, the process is not commercially feasible because of the high costs of the metals and the flamable ether usage (N. Auner and J. Grobe, J. Organometal. Chem., 188(1980), 151).

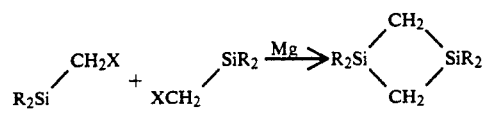

In 1966, Nametkin and his co-workers reported that 1,3-disilacyclobutanes were obtained from the pyrolysis of monosilacyclobutanes. The thermolysis of monosilacyclobutanes gives off ethylene gas and silene intermediates which are dimerized to 1,3-disilacyclobutanes. Monosilacyclobutanes are not commercially available but are prepared by Grignard reactions (N. S. Nametkin, V. M. Vdovin, L. E. Gusel'nikov, and V. I. Zav'yallov, Izv. Akad. Nauk. SSSR, Ser. Khim., 584(1966)).

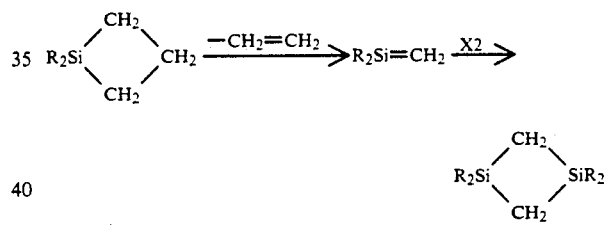

In 1977, Jones and his co-workers reported that 1,3-disilacyclobutanes were obtained from the reaction of tert-butyllithium with vinylchlorosilanes. Tert-buthyllithium is added to the vinyl group of the silane, followed by lithium chloride elimination to give a silene, which is dimerized to 1,3-disilacyclobutane (P. R. Jones and T. F. O. Lim, J. Am. Chem. Soc., 99, 2013(1977)).

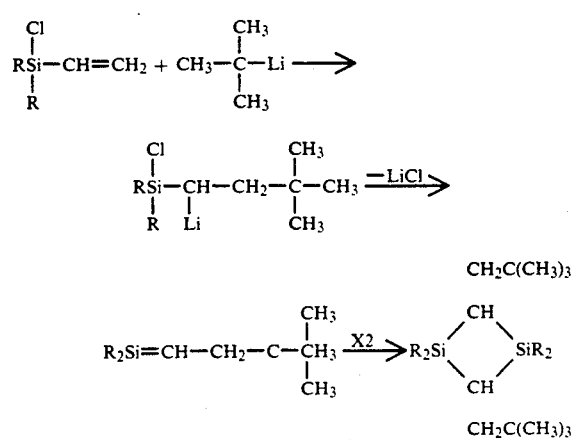

In 1983, Barton and his co-workers reported that 1,3-disilacyclobutanes were obtained from the thermolysis of monosilacyclobutanes having 1-(trimethylsilyl)-methyl group. In the silenes generated through the extrusion of ethylene are proceeded 1,5-hydrogen shift and followed by the intramolecular ring closure of the biradicals to give 1,3-disilacyclobutanes (J. Barton, G. T. Burns, and D. Gschneidner, Organometallics, 1983, 2, 8).

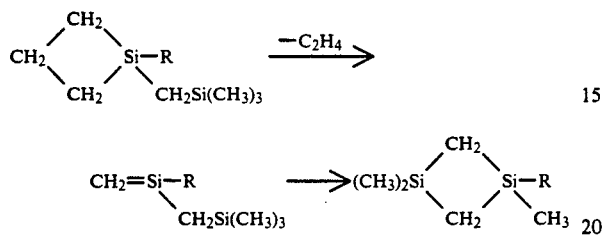

The starting materials used in the above reaction are not commercially available and must be prepared by Grignard reactions. This is why it has not drawn much attention in commercial utilizations.

The present inventors recently reported the preparation methods of trisilaalkanes as represented by the formula(IV) by the direct reactions of silicon with silanes having chloromethyl group as represented by formula(III) in the presence of a copper catalyst (Korean Patent application Number 91-1055).

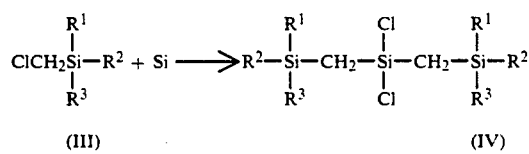

Wherein $R^1$, $R^2$, and $R^3$ are independently methyl or chlorine atom.

Organochlorosilanes are easily reacted with alcohols to give alkoxysilanes (Noll, "Chemistry and Technology of Silicones", Academic Press, New York, 1968). Chlorotrisilaalkanes as represented by formula (IV) can be reacted with methanol and easily converted to the corresponding methoxytrisilaalkanes as represented by formula(II). Since compounds of formula(IV) have two chlorine atoms on the center silicon atom, one of them can be replaced by an organic group using Grignard reagents as represented in formula(V) and then the other chlorine may be reacted with an alcohol.

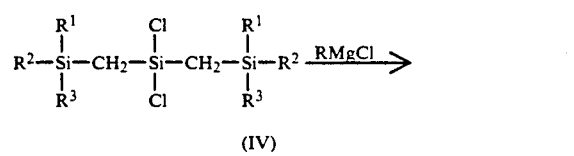

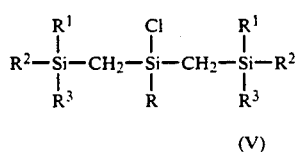

In formula(V), $R^1$, $R^2$, and $R^3$ can be independently methyl, methoxy, or chlorine atom and R is phenyl or methyl.

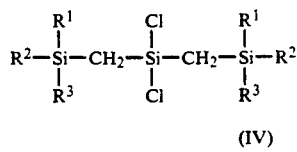

or

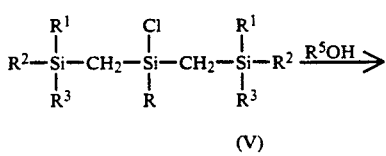

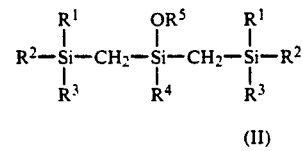

In formula (II), $R^1$, $R^2$, and $R^3$ can be independently methyl, methoxy, or chlorine atom and $R^5$ is phenyl or methyl.

It is well known in the art that organomethoxysilanes having a trimethylsilyl group at the alpha carbon undergoes beta elimination of trimethylmethoxysilane to produce silenes upon thermolysis(T. J. Barton, G. T. Burns, E. V. Arnold, and J. C. Clardy, Terahedron Lett., 1981, 22, 7).

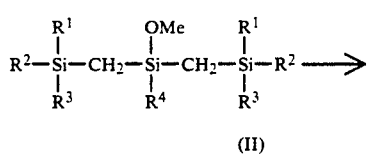

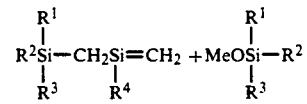

In the present invention, alkoxytrisilaalkanes as represented by the formula (II) have been prepared by reacting the corresponding chlorotrisilaalkanes as represented by the formula(IV) with alcohols such as methanol or ethanol. Chloro-2,4,6-trisilaheptanes, wherein at least one of $R^1$, $R^2$, or $R^3$ is a methyl group, and chloro-1,3,5-trisilapentanes, wherein $R^1$, $R^2$, and $R^3$ are all methyl groups, have been converted to the corresponding alkoxy compounds by alcoholysis. In some cases, one of the two chlorines on the center silicon of the trisilaalkanes was treated with a Grignard reagent as represented by formula (V) to give trisilaalkane compounds substituted with an organic group on the center silicon, before they were reacted with alcohols. The alkoxytrisilaalkanes prepared in this invention are listed in Table 1.

TABLE 1

| | Chlorotrisilaalkanes (Formula IV) | | | RMgCl | | R⁵OH | | Alkoxytrisilaalkanes prepared | | | | Yields | bp |
|---|---|---|---|---|---|---|---|---|---|---|---|---|---|
| Exp. | $R^1$ | $R^2$ | $R^3$ | R | Amt. (mole) | $R^5$ | Amt. (mole) | $R^1$ | $R^2$ | $R^3$ | $R^4$ | (%) | (°C./Torr) |
| 1 | Me | Me | Me | Ph | 1 | Me | 1 | Me | Me | Me | Ph | 84 | 175–177/20 |
| 2 | Me | Me | Me | Me | 1 | Me | 1 | Me | Me | Me | Me | 79 | 104–105/20 |
| 3 | Me | Me | Me |  |  | Me | 2 | Me | Me | Me | OMe | 86 | 104–105/28 |
| 5 | Cl | Me | Me |  |  | Me | 4 | OMe | Me | Me | OMe | 87 | 124–126/33 |
| 6 | Cl | Cl | Me |  |  | Me | 6 | OMe | OMe | Me | OMe | 84 | 136–139/20 |
| 7 | Cl | Cl | Cl |  |  | Me | 8 | OMe | OMe | OMe | OMe | 82 | 136–142/20 |
| 8 | Me | Me | Me |  |  | Me | 1 | Me | Cl | Me | Cl | 73 | 110–116/20 |
| 9 | Cl | Cl | Me |  |  | Me | 1 | Cl, OMe | OMe | Me | Cl | 65 | 112–118/20 |
| 10 | Cl | Cl | Cl |  |  | Me | 3 | OMe | Cl | Me | Cl | 62 | 126–132/20 |
| 11 | Cl | Cl | Cl |  |  | Me | 5 | OMe | Cl | OMe | Cl | 58 | 138–145/20 |
| 12 | Cl | Cl | Cl |  |  | Et | 5 | OEt | Cl | OEt | Cl | 52 | 175–183/20 |

1,3-Disilacyclobutanes as represented by the formula (I) were obtained by pyrolyzing the alkoxytrisilaalkanes (II) extruding alkoxysilane as represented by the formula (VI) at a temperature from 400° C. to 800° C., at atmospheric pressure or under a vacuum. The compositions of the products of the pyrolysis at various reaction conditions are shown in Table 2.

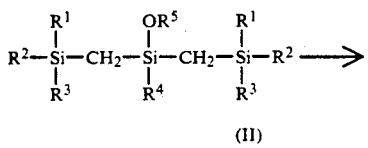

(II)

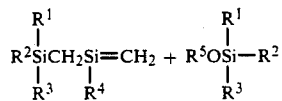

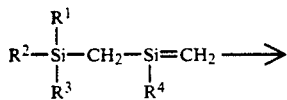

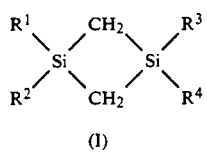

(I)

wherein $R^1$, $R^2$, $R^3$, $R^4$, and $R^5$ can be independently methyl, methoxy, ethoxy, or phenyl.

The invention is illustrated in the greater detail in the following examples which are not intended as limitations thereof.

EXAMPLE 1

Preparation of 2,2,6,6-tetramethyl-4-phenyl-2,4,6-trisilaheptane

To a dried 250 ml round bottomed flask equipped with a reflux condenser and a dropping funnel was added 2,2,6,6-tetramethyl-4,4-dichloro-2,4,6-trisilaheptane 13.7 g(50 mmole) under nitrogen gas. 25 ml of Phenyl Grignard reagent(2M sol. in THF) was then added dropwise to the solution with stirring. After additional stirring for one hour to complete the reaction, 16 ml of sodium methoxide solution prepared from 1.2 g(52.2 mmole) of sodium metal and methanol was added dropwise through the funnel. After completing the addition, the solution was refluxed for 30 min.

After the reaction was completed, 50 ml of hexane was added to the solution and the solid was filtered. After evaporating the low boilers, the vacuum distillation at 70 mm Hg gave 13.1 g(84% yield) of 2,2,6,6-tetramethyl-4-methoxy-4-phenyl-2,4,6-trisilaheptane at 175°–179° C.

1H-NMR(CDCl₃, ppm), 0.00(s, 18H, SiMe₃), 0.18(s, 4H, SiCH₂Si), 7.35–7.38, 7.56–7.58(brd m, 5H, SiPh).

EXAMPLE 2

Preparation of 2,2,4,6,6-pentamethyl-4-methoxy-2,4,6-trisilaheptane

The reaction was carried out under the same conditions as Example 1 except that methyl Grinard reagent

TABLE 2

| | Alkoxytrisilaalkanes Formula II | | | | | Reacts. | Products | Recovery | Decomp. | Product Compd. (I) | |
|---|---|---|---|---|---|---|---|---|---|---|---|
| Exp. | $R^1$ | $R^2$ | $R^3$ | $R^4$ | $R^5$ | (g) | (g) | (%) | (%) | Yields (%) | Remark |
| 13 | Me | Me | Me | OMe | Me | 6.6 | 4.6 | 70 | 96 | 30 | |
| 14 | OMe | Me | Me | OMe | Me | 8.8 | 6.4 | 73 | 96 | 36 | |
| 15 | OMe | OMe | Me | OMe | Me | 14.9 | 11.7 | 79 | 88 | 32 | |
| 16 | OMe | OMe | OMe | OMe | Me | 5.8 | 3.8 | 66 | 82 | 15 | |
| 17 | Me | Me | Me | Cl | Me | 9.1 | 7.6 | 83 | 38 | 20 | |
| 18 | OMe | Cl | Me | Cl | Me | 8.2 | 7.0 | 85 | 43 | 20 | |
| 19 | OMe | Cl | OMe | Cl | Me | 7.3 | 5.7 | 78 | 56 | 25 | |
| 20 | OEt | Cl | OEt | Cl | Et | 9.3 | 8.1 | 87 | 43 | 27 | |
| 21 | Cl, OMe | Me | Me | Cl | Me | 6.7 | 5.5 | 82 | 41 | 15 | |
| 22 | Me | Me | Me | Ph | Me | 6.0 | 4.2 | 69 | 59 | 32 | |
| 23 | Me | Me | Me | Me | 5.6 | 4.2 | 75 | 58 | 14 | | |
| 24 | Me | Me | Me | OMe | Me | 8.2 | 7.0 | 85 | 52 | 27 | 450° C. |
| 25 | OMe | OMe | Me | OMe | Me | 7.6 | 4.4 | 58 | 98 | 13 | 750° C. |
| 26 | Me | Me | Me | OMe | Me | 8.4 | 6.8 | 81 | 95 | 33 | under vacuum | solution(17 ml, 51 mmole, 3M solution in THF) was used instead of phenyl Grignard reagent to obtain 10.1 g(79% yield) of 2,2,4,6,6-pentamethyl-4-methoxy-2,4,6-trisilaphetane.

bp 104°–105° C./28 torr, $^1$H-NMR(CDCl$_3$), $\delta$ −0.18(d, 2H SiCH$_2$Si, J$_{gem}$=14.26 Hz), −0.08(d, 2H, SiCH$_2$Si, J$_{gem}$=14.26 Hz), 0.05(s, 3H, SiCH$_3$), 3.38(s, 3H, SiOCH$_3$).

EXAMPLE 3

Preparation of 2,2,6,6-tetramethyl-4,4-dimethoxy-2,4,6-trisilaheptane 3.7 g (50 mmol) of 2,2,6,6-tetramethyl-4,4-dichloro-2,4,6-trisilaheptane was placed in the flask and then through the dropping funnel were dropwisely added 3.5 g(109 mmole) of methanol and followed by 8.6 g(109 mmole) of pyridine, as described in Example 1. At the end of addition, the mixture was heated to reflux for 30 minutes to complete the reaction. 50 ml of hexane was added therein, and then the solid was filtered off. The remaining solution was solvent evaporated and was distilled under reduced pressure to obtain 10.5 g(87% yield) of 2,2,6,6-tetramethyl-4,4-dimethoxy-2,4,6-trisilaheptane.

bp 104°–105° C./20 torr, $^1$H-NMR(CDCl$_3$), $\delta$ −0.17(s, 4H, SiCH$_2$Si), 0.44(s, 18H, SiCH$_3$), 3.44(s, 6H, SiOCH$_3$).

EXAMPLE 4

Preparation of 2,2,6,6-tetramethyl-4,4-dimethoxy-2,4,6-trisilaheptane

The reaction was carried out under the same conditions as Example 3 except that the same moles of triethyl amine were used instead of pyridine. The amount of the product was 12 g and the yield 77.3%.

EXAMPLE 5

Preparation of 2,6-dimethyl-2,4,4,6-tetramethoxy-2,4,6-trisilaheptane

The reaction was carried out under the same conditions as Example 3 except that instead of 2,2,6,6-tetramethyl-4,4-dichloro-2,4,6-trisilaheptane was used 50 mmole of 2,6-dimethyl-2,4,4,6-tetrachlorotrisilaheptane was used 50 mmole of 2,6-dimethyl-2,4,4,6-tetrachloro-2,4,6-trisilaheptane, and also were used methanol and pyridine in 220 mmoles and 200 mmoles respectively. The amount of the product was 13.2 g and the yield 87%.

bp 124°–126° C./33 torr, $^1$H-NMR(CDCl$_3$), $\delta$0.03(s, 4H, SiCH$_2$Si), 0.16(s, 12H, SiCH$_3$), 3.41(s, 6H, SiOCH$_3$), 3.48(s, 6H, SiOCH$_3$).

EXAMPLE 6

Preparation of 2,2,4,4,6,6-hexamethoxy-2,4,6-trisilaheptane 21.7 g(60 mmoles) of 2,2,4,4,6,6-hexachloro-2,4,6-trisilaheptane were placed in the flask of the same set as Example 1 and then through the dropping funnel was dropwisely added sodium methoxide synthesized from 8.8 g(380 mmoles) of sodium in 20 ml of dry methanol. At the end of addition, the mixture was heated to reflux for 30 minutes to complete the reaction, 150 ml of hexane was added therein, and then the solid was filtered off. The remaining solution was solvent evaporated and was distilled under reduced pressure to obtain 16.5 g(84% yield) of 2,2,4,4,6,6-hexamethoxy-2,4,6-trisilaheptane.

bp 131°–139° C./20 torr, $^1$H-NMR(CDCl$_3$), $\delta$0.08(s, 4H, SiCH$_2$Si), 0.18(s, 6H, SiCH$_3$), 3.51(s, 18H, SiOCH$_3$).

EXAMPLE 7

Preparation of 1,1,1,3,3,5,5,5-octamethoxy-1,3,5-trisilaheptane

The reaction was carried out under the same conditions as Example 6 except that instead of 2,2,4,4,6,6-hexachloro-2,4,6-trisilaheptane was used 19.8 g(50 mmoles) of 1,1,1,3,3,5,5,5-octachloro-1,3,5-trisilaheptane, and the mixture was reacted with 460 mmoles of sodium methoxide. The amount of the product was 14.8 g and the yield 82%.

bp 136°–142° C./20 torr, $^1$H-NMR(CDCl$_3$), $\delta$0.09(s, 4H, SiCH$_2$Si), 3.54(s, 6H, SiOCH$_3$), 3.57(s, 18H, SiOCH$_3$).

EXAMPLE 8

Preparation of 2,2,6,6-tetramethyl-4-chloro-4-methoxy-2,4,6-trisilaheptane 13.7 g(50 mmoles) of 2,2,6,6-tetramethyl-4,4-dichloro-2,4,6-trisilaheptane were placed in the flask of the same set as Example 1, and then 1.8 g(60 mmoles) of dry methanol were added. The mixture was heated at 70° C. for 2 hrs. The amount of the product was 9.92 g and the yield 74%.

bp 110°–116° C./20 torr, $^1$H-NMR(CDCl$_3$), $\delta$0.18(s, 4H, SiCH$_2$Si), 0.11 (s, 18, SiCH$_3$), 3.50(s, 3H, SiOCH$_3$).

EXAMPLE 9

Preparation of 2,6-dimethyl-2,4-dimethoxy-4,6-dichloro-2,4,6-trisilaheptane 15.7 g(50 mmoles) of 2,6-dimethyl-2,4,4,6-tetrachloro-2,4,6-trisilaheptane were placed in the flask of the same set as Example 8. The mixture was heated at 70° C. for 2 hrs, after adding 3.5 g(110 mmoles) of dry methanol. The amount of the product was 9.95 g and the yield 65%.

bp 112°–118° C./20 torr, $^1$H-NMR(CDCl$_3$), $\delta$0.18(s, 2H, SiCH$_2$Si), 0.28(s, 2H, SiCH$_2$Si), 0.21(s, 6H, SiCH$_3$), 0.95(s, 6H, SiCH$_3$), 3.48(s, 3H, SiOCH$_3$), 3.53(s, 3H, SiOCH$_3$).

EXAMPLE 10

Preparation of 2,4,6-trimethoxy-2,4,6-trichloro-2,4,6-trisilaheptane 17.8 g(50 mmoles) of 2,2,4,4,6,6-hexachloro-2,4,6-trisilaheptane were placed in the flask of the same set as Example 1. The mixture was heated at 70° C. for 3 hrs, after adding 5.5 g(170 mmoles) of dry methanol. The amount of the reaction product was 10.6 g and the yield 62%.

bp 126°–132° C./20 torr, $^1$H-NMR(CDCl$_3$), $\delta$0.32(s, 4H, SiCH$_2$Si), 0.96(s, 6H, SiCH$_3$), 3.52(s, 6H, SiOCH$_3$), 3.57(s, 3H, SiOCH$_3$).

EXAMPLE 11

Preparation of
1,1,3,5,5-pentamethoxy-1,3,5-trichloro-1,3,5-trisilaheptane 15.8 g(40 mmoles) of 1,1,1,3,3,5,5,5-octachloro-1,3,5-trisilapentane were placed in the flask of the same set as Example 1. The mixture was heated at 70° C. for 3 hrs, after adding 9.3 g(290 mmoles) of dry methanol. The amount of the reaction product was 8.7 g and the yield 58%.

bp 138°–145° C./20 torr, $^1$H-NMR(CDCl$_3$), δ0.35(s, 4H, SiCH$_2$Si), 3.57(s, 12H, SiOCH$_3$), 3.62(s, 3H, SiOCH$_3$).

EXAMPLE 12

Preparation of
1,1,3,5,5-pentaethoxy-1,3,5-trichloro-1,3,5-trisilaheptane 15.8 g(40 mmoles) of 1,1,1,3,3,5,5,5-octachloro-1,3,5-trisilapentane were placed in the flask of the same set as Example 1. The mixture was heated at 70° C. for 3 hrs, after adding 13.8 g(300 mmoles) of dry ethanol. The amount of the reaction product was 9.4 g and the yield 52%.

bp 175°–183° C./20 torr, $^1$H-NMR(CDCl$_3$), δ0.33(s, 4H, SiCH$_2$Si), 1.4–1.6(s, 15H, SiOCH$_2$CH$_3$), 3.3–3.5(m, 10H, SiOCH$_2$CH$_3$).

EXAMPLE 13

Pyrolysis of
2,2,6,6-tetramethyl-4,4-dimethoxy-2,4,6-trisilaheptane

A heating wire was wound outside wall of a quartz glass column being 18 mm inner diameter and 300 mm length by 250 mm in the length. The quartz glass column was filled inside with pieces of quartz glass. A pyrex glass column having the same diameter was connected on the top part of the quartz glass column, a glass joint was fixed at the end of the pyrex glass column and then a rubber stopper was plugged. A fine teflon needle was connected through the rubber stropper and then samples were injected at certain flow rate by a syringe pumb. A glass column having 7 mm diameter was side-fixed under the joint to connect with a nitrogen tank. The connecting part of the pyrex glass column with the quartz glass column was filled again with pieces of quartz glass by 100 mm and with the heating wire was wound outside wall thereof to heat to 200° C. Thus, the samples were preheated to evaporate and the vaporized samples were passing through the reaction bath heated to the temperature from 400° to 800° C. to carry out the pyrolysis. It was preferred to flow some nitrogen gas, in order to effect the flow of samples or products. A trap was connected under the quartz glass column, which was capable of equipping with incubation bath of liquid nitrogen, so that the products could be collected. The area venting nitrogen gas was also connected with a set preventing countercurrent of oils.

Pyrolysis

The quartz glass column was heated to 625° C. and then the nitrogen gas was flowed therein at the rate of 120 ml per minute. After the inside of the pyrolysis set was silylated by slowly flowing 1,1,1,3,3,3-hexamethyldisilazane(200–300 μl) inside the quartz glass column and was seasoned, the nitrogen gas was flowed for 1 hour to remove the residue in the pyrolysis set. The trap connected with the under part of the quartz glass column was cooled with the incubation bath of liquid nitrogen, and then 2,2,6,6-tetramethyl-4,4-dimethoxy-2,4,6-trisilaheptane(6.6 g, 26 mmol) to be pyrolyzed was placed in the Gas tight syringe and was injected inside the quartz glass column at a certain rate, using the syringe pump.

All the amounts of the pyrolysis products collected in two trap which completed pyrolysis were recovered to measure. The result was 4.6 g, being 70% as the mass recovery rate. To analyze these by the capillary gas chromatography, the resolution rate was 98%. Each product was distilled to confirm as 2.3 g (50%) of trimethylmethoxysilane and 1.4 g(30%) of 1,3,3-trimethyl-1-methoxy-1,3-disilacyclobutane.

$^1$H-NMR(CDCl$_3$), δ0.23(s, 4H, SiCH$_2$Si), 0.27(s, 9H, SiCH$_3$), 3.48(s, 3H, SiOCH$_3$).

EXAMPLE 14

Pyrolysis of
2,6-dimethyl-2,4,4,6-tetramethoxy-2,4,6-trisilaheptane

The pyrolysis was carried out under the same conditions as Example 13 using the same set, except that 8.8 g(30 mmol) of 2,6-dimethyl-2,4,4,6-tetramethoxy-2,4,6-trisilaheptane was used instead of 2,2,6,6-tetramethyl-4,4-dimethoxy-2,4,6-trisilaheptane. All the recovered reaction products were 6.4 g, being 73% as the mass recovery rate and 93% as the resolution rate. As the results of confirming each product which was distilled, 2.3 g(38%) of dimethyldimethoxysilan and 2.2 g(36%) of 1,3-dimethyl-1,3-dimethoxy-1,3-disilacyclobutane were obtained.

$^1$H-NMR(CDCl$_3$), δ0.27(s, 6H, SiCH$_2$Si), 0.37(s, 4H, SiCH$_2$Si), 3.55(s, 6H, SiOCH$_3$).

EXAMPLE 15

Pyrolysis of
2,2,4,4,6,6-hexamethoxy-2,4,6-trisilaheptane

The pyrolysis was carried out under the same conditions as Example 13 using the same set, except that 14.9 g(45 mmol) of 2,2,4,4,6,6-hexamethoxy-2,4,6-trisilaheptane was used instead of 2,2,6,6-tetramethyl-4,4-dimethoxy-2,4,6-trisilaheptane. All the recovered reaction products were 11.7 g, being 79% as the mass recovery rate and 88% as the resolution rate. As the results of confirming each product which was distilled, 4.0 g(39%) of methyltrimethoxysilane and 3.3 g(32%) of 1-methyl-1,3,3-trimethoxy-1,3-disilacyclobutane were obtained.

$^1$H-NMR(CDCl$_3$), δ0.37(s, 6H, SiCH$_3$), 0.43(d, 2H, SiCH$_2$Si, J=16.4 Hz), 0.62(d, 2H, SiCH$_2$Si, J=16.4 Hz), 3.49, 3.55, 3.58(s, 9H, SiOCH$_3$).

EXAMPLE 16

Pyrolysis of
1,1,1,3,3,5,5,5-octamethoxy-1,3,5-trisilaheptane

The pyrolysis was carried out under the same conditions as Example 13 using the same set, except that 5.8 g(16 mmol) of 1,1,1,3,3,5,5,5-octamethoxy-1,3,5-trisilapentane was used instead of 2,2,6,6-tetramethyl-4,4-dimethoxy-2,4,6-trisilaheptane. All the recovered reaction products were 3.6 g, being 66% as the mass recovery rate and 82% as the resolution rate. As the results of confirming each product which was distilled, 0.6 g(20%) of tetramethoxysilane and 0.5 g(15%) of 1,1,3,3-tetramethoxy-1,3-disilacyclobutane were obtained.

$^1$H-NMR(CDCl$_3$), $\delta$0.61(s, 4H, SiCH$_2$Si), 3.59(s, 3H, SiOCH$_3$).

EXAMPLE 17

Pyrolysis of 2,2,6,6-tetramethyl-4-methoxy-4-chloro-2,4,6-trisilaheptane

The pyrolysis was carried out under the same conditions as Example 13 using the same set, except that 9.1 g(34 mmol) of 2,2,6,6-tetramethyl-4-methoxy-4-chloro-2,4,6-trisilaheptane was used instead of 2,2,6,6-tetramethyl-4,4-dimethoxy-2,4,6-trisilaheptane. All the recovered reaction products were 7.6 g, being 83% as the mass recovery rate and 38% as the resolution rate. As the results of confirming each product which was distilled, 0.9 g(32%) of trimethylchlorosilane and 0.5 g(20%) of 1,3,3-trimethyl-1-chloro-1,3-disilacyclobutane were obtained.

$^1$H-NMR(CDCl$_3$), $\delta$0.53–0.47(d, 2H, SiCH$_2$Si, J=18 Hz), 0.62–0.57(d, 2H, SiCH$_2$Si, J=18 Hz), 0.64(s, 3H, SiCH$_3$), 0.36(s, 3H, SiCH$_3$), 0.27(s, 3H, SiCH$_3$).

EXAMPLE 18

Pyrolysis of 2,4,6-trimethoxy-2,4,6-trichloro-2,4,6-trisilaheptane

The pyrolysis was carried out under the same conditions as Example 13 using the same set, except that 8.2 g(24 mmol) of 2,4,6-trimethoxy-2,4,6-trisilaheptane was used instead of 2,2,6,6-tetramethyl-4,4-dimethoxy-2,4,6-trisilaheptane. All the recovered reaction products were 7.0 g, being 85% as the mass recovery rate and 43% as the resolution rate. As the results of confirming each product which was distilled, 0.9 g(28%) of methyltrimethoxysilane and 0.8 g(20%) of 1-methyl-3-methoxy-1,3-disilacyclobutane were obtained.

$^1$H-NMR(CDCl$_3$), $\delta$3.65(s, 2H, SiOCH$_3$), 0.82(s, 4H, SiCH$_2$Si), 0.67 (s, 3H, SiCH$_3$).

EXAMPLE 19

Pyrolysis of 1,1,3,5,5-pentamethoxy-1,3,5-trichloro-1,2,3-trisilapentane

The pyrolysis was carried out under the same conditions as Example 13 using the same set, except that 7.3 g(20 mmol) of 1,1,3,5,5-pentamethoxy-1,3,5-trichloro-1,3,5-trisilapentane was used instead of 2,2,6,6-tetramethyl-4,4-dimethoxy-2,4,6-trisilaheptane. All the recovered reaction products were 5.7 g, being 78% as the mass recovery rate and 56% as the resolution rate. As the results of confirming each product which was distilled, 1.1 g(35%) of trimethoxysilane and 0.8 g(25%) of 1,3-dimethoxy-1,3-dichloro-1,3-disilacyclobutane were obtained.

$^1$H-NMR(CDCl$_3$), $\delta$3.68(s, 6H, SiOCH$_3$), 0.98(s, 4H, SiCH$_2$Si).

EXAMPLE 20

Pyrolysis of 1,1,3,5,5-pentaethoxy-1,3,5-trichloro-1,3,5-trisilapentane

The pyrolysis was carried out under the same conditions as Example 13 using the same set, except that 9.3 g(22 mmol) of 1,1,3,5,5-pentaethoxy-1,3,5-trichloro-1,3,5-trisilapentane was used instead of 2,2,6,6-tetramethyl-4,4-dimethoxy-2,4,6-trisilaheptane. All the recovered reaction products were 8.1 g, being 87% as the mass recovery rate and 48% as the resolution rate. As the results of confirming each product which was distilled, 1.0 g(28%) of triethylchlorosilane and 0.9 g(27%) of 1,3-diethoxy-1,3-dichloro-1,3-disilacyclobutane were obtained.

$^1$H-NMR(CDCl$_3$), $\delta$3.70(t, 4H, SiOCH$_2$CH$_3$), 1.23(d, 6H, SiOCH$_2$CH$_3$), 0.67(s, 3H, SiCH$_2$Si)

EXAMPLE 21

Pyrolysis of 2,6-dimethyl-2,4-dimethoxy-4,6-dichloro-2,4,6-trisilaheptane

The pyrolysis was carried out under the same conditions as Example 13 using the same set, except that 6.7 g(22 mmol) of 2,6-dimethyl-2,4-dimethoxy-4,6-dichloro-2,4,6-trisilaheptane was used instead of 2,2,6,6-tetramethyl-4,4-dimethoxy-2,4,6-trisilaheptane. All the recovery reaction products were 5.5 g, being 82% as the mass recovery rate and 41% as the resolution rate. As the results of confirming each product which was distilled, 0.6 g(18%) of dimethyldimethoxysilane and 0.2 g(10%) of 1,3-dimethyl-1,3-dichloro-1,3-disilacyclobutane were obtained.

$^1$H-NMR(CDCl$_3$), $\delta$0.79(s, 4H, SiCH$_2$Si), 0.69(s, 6H, SiCH$_3$)

EXAMPLE 22

Pyrolysis of 2,2,6,6-tetramethyl-4-methoxy-4-phenyl-2,4,6-trisilaheptane

The pyrolysis was carried out under the same conditions as Example 13 using the same set, except that 6.0 g(16 mmol) of 2,2,6,6-tetramethyl-4-methoxy-4-phenyl-2,4,6-trisilaheptane was used instead of 2,2,6,6-tetramethyl-4,4-dimethoxy-2,4,6-trisilaheptane. All the recovered reaction products were 4.2g, being 69% as the mass recovery rate and 59% as the resolution rate. As the results of confirming each product which was distilled, 0.6 g(23%) of trimethylmethoxysilane and 0.8 g(32%) of 1,3,3-trimethyl-1-phenyl-1,3-disilacyclobutane were obtained.

$^1$H-NMR(CDCl$_3$), $\delta$0.33(d, 2H, SiCH$_2$Si, J=16.4 Hz), 0.24(d, 2H, SiCH$_2$Si, J=16.4 Hz), 0.24(s, 3H, SiCH$_3$), 0.34(s, 3H, SiCH$_3$), 0.48(s, 3H, SiCH$_3$), 7.37–7.61(m, 5H, SiPh).

EXAMPLE 23

Pyrolysis of 2,2,4,6,6-pentamethyl-4-methoxy-2,4,6-trisilaheptane

The pyrolysis was carried out under the same conditions as Example 13 using the same set, except that 5.6 g(23 mmol) of 2,2,4,6,6-pentamethyl-4-methoxy-2,4,6-trisilaheptane was used instead of 2,2,6,6-tetramethyl-4,4-dimethoxy-2,4,6-trisilaheptane. All the recovered reaction products were 4.2 g, being 75% as the mass recovery rate and 58% as the resolution rate. As the results of confirming each product which was distilled, 0.9 g(38%) of trimethylmethoxysilane and 0.3 g(14%) of 1,1,3,3-tetramethyl-1,3-disilacyclobutane were obtained.

EXAMPLE 24

Pyrolysis of 2,2,6,6-tetramethyl-4,4-dimethoxy-2,4,6-trisilaheptane

The reactant of Example 13 was reacted under the same conditions as Example 13 using the same set, except that the reaction temperature was lowered to 450° C., and 8.2 g(31 mmol) of the reactant was used. All the recovered reaction products were 7.0 g, being 87% as the mass recovery rate and 52% as the resolution rate. As the results of confirming each product which was distilled, 1.9 g(45%) of trimethylmethoxysilane and 1.1 g(27%) of 1,3,3-trimethyl-1-methoxy-1,3-disilacyclobutane were obtained.

EXAMPLE 25

Pyrolysis of 2,2,4,4,6,6-hexamethoxy-2,4,6-trisilaheptane

The reactant of Example 15 was reacted under the same conditions as Example 15 using the same set, except that the reaction temperature was raised to 750° C., and 7.6 g(23 mmol) of the reactant was used. All the recovered reaction products were 4.4 g, being 58% as the mass recovery rate and 98% as the resolution rate. As the results of confirming each product which was distilled, 2.4 g(55%) of methyltrimethoxysilane and 0.6 g(13%) of 1-methyl-1,3,3-trimethoxy-1,3-disilacyclobutane.

EXAMPLE 26

Pyrolysis of 2,2,6,6-tetramethyl-4,4-dimethoxy-2,4,6-trisilaheptane 8.4 g(32 mmol) of 2,2,6,6-tetramethyl-4,4-dimethoxy-2,4,6-trisilaheptane in Example 13 was reacted at the same temperature as Example 13 using the same reaction set, except that nitrogen was not flowed, and the inside of the reactor was maintained under the vacuum of about $10^{-3}$ torr. All the reaction products recovered after the reaction were 6.8 g, being 81% as the mass recovery rate. 2.2 g(33%) of 1,1,3-trimethyl-3-methoxy-1,3-disilacyclobutane was obtained.

What is claimed is:

1. A 1,3-disilacyclobutane compound having the formula:

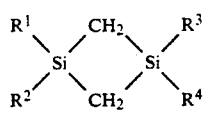

wherein $R^1$, $R^2$, $R^3$ and $R^4$ are methoxy groups.

2. A 1,3-disilacyclobutane compound having the formula:

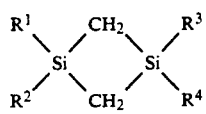

wherein $R^1$ and $R^4$ are methoxy groups and $R^2$ and $R^3$ are chloro groups.

3. A 1,3-disilacyclobutane compound having the formula:

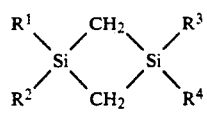

wherein $R^1$ and $R^4$ are ethoxy groups and $R^2$ and $R^3$ are chloro groups.

4. A process for the preparation of 1,3-disilacyclobutanes as represented by Formula I which comprises pyrolyzing alkoxytrisilaalkane derivatives as represented by Formula II at a temperature from 400° C. to 800° C. at atmospheric pressure or under a vacuum.

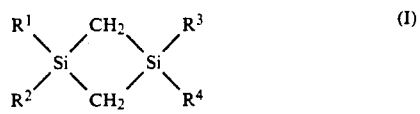

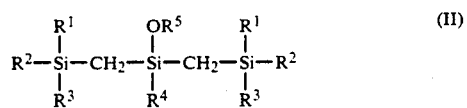

wherein $R^1$, $R^2$, $R^3$, $R^4$ and $R^5$ are members independently selected from the group consisting of methyl, methoxy, ethoxy and phenyl.

* * * * *